United States Patent [19]

Truesdell

[11] Patent Number: 4,652,266
[45] Date of Patent: Mar. 24, 1987

[54] MOLDED ELASTOMERIC PROSTHETIC FOOT HAVING ENERGY-STORING ARTICULATED KEEL

[75] Inventor: James D. Truesdell, Corona Del Mar, Calif.

[73] Assignee: Kingsley Mfg. Co., Placentia, Calif.

[21] Appl. No.: 837,398

[22] Filed: Mar. 7, 1986

[51] Int. Cl.[4] ............................................. A61F 2/66
[52] U.S. Cl. ............................................. 623/55
[58] Field of Search ............................ 623/53-56

[56] References Cited

U.S. PATENT DOCUMENTS

| | | |
|---|---|---|
| 468,352 | 2/1892 | Linkert . |
| 977,974 | 12/1910 | Showalter . |
| 1,104,413 | 7/1914 | Conner et al. . |
| 2,692,392 | 4/1951 | Bennington et al. . |
| 3,098,239 | 1/1961 | Nader . |
| 3,484,871 | 12/1968 | Orange . |
| 3,766,569 | 10/1973 | Orange . |
| 3,833,941 | 9/1974 | Wagner . |
| 3,982,280 | 9/1976 | Ashelle et al. ............ 623/55 |
| 4,091,472 | 5/1978 | Daher et al. . |
| 4,177,525 | 12/1979 | Arbogast et al. . |
| 4,328,594 | 5/1982 | Campbell . |
| 4,360,931 | 11/1982 | Hampton ...................... 623/55 |

FOREIGN PATENT DOCUMENTS

| | | | |
|---|---|---|---|
| 17896 | 12/1934 | Australia ............................ 623/53 |
| 326131 | 9/1920 | Fed. Rep. of Germany . |
| 817186 | 10/1951 | Fed. Rep. of Germany ........ 623/53 |
| 22533 | 7/1927 | France ................................ 623/53 |
| 2293186 | 7/1976 | France . |

OTHER PUBLICATIONS

Edwards, J. W., "Orthopaedic Appliances Atlas, vol. 2, Artificial Limbs," pp. 129, 138-141, 148-161.
Brochure entitled, "The Seattle Foot," by Model & Instrument Works, Inc., Seattle, Wash.
Brochure entitled, "The Seattle Foot Development Status".
Brochure entitled, "Product Catalog", by Campbell Childs, Inc., 1983.

*Primary Examiner*—Richard J. Apley
*Assistant Examiner*—James Prizant
*Attorney, Agent, or Firm*—Gausewitz, Carr & Rothenberg

[57] ABSTRACT

A prosthetic foot is disclosed which comprises an articulated heel. The heel comprises a plurality of links and has energy-storing resilient devices at adjacent ends of the links.

28 Claims, 6 Drawing Figures

MOLDED ELASTOMERIC PROSTHETIC FOOT HAVING ENERGY-STORING ARTICULATED KEEL

BACKGROUND OF THE INVENTION

Since the introduction of artificial limbs, prosthetic feet have taken on various forms and functions. Many of the foot concepts have been patented. However, only a few of such concepts have been embraced by the limb-fitting profession and in turn accepted by the ultimate consumer—the leg amputee. Until about 1950, the most popular style of foot in use was an articulated-ankle type that allowed the foot to simulate, on a limited basis, the plantar flexion (ball of the foot contacting the walking surface immediatley after heel contact) and dorsiflexion (the lower leg progressing forwardly to a predetermined angle before the heel lifts off the ground) actions of the normal ankle. There were also a few brands of solid rubber feet utilizing an internal core structure, called a "keel", of wood or metal. The keel furnished an attachment by which the foot could be anchored solidly to the leg, there being no articulated ankle. The heel area was also solid rubber, and this made it difficult for the amputee to walk comfortably, for there would be a jolt upon heel contact with the ground. Consequently, most amputees developed a distinctive compensating gait.

World War II brought about a surge in prosthetic research by the U.S. Government, both directly within service hospitals and through grants to universities and individual firms. One of the results of this research was the development, in the 1950s, of an economically-feasible production foot by the University of California Engineering Department in cooperation with a U.S. naval hospital. This foot was widely accepted worldwide, so much as that the articulated ankle foot was largely rendered obsolete. The University of California foot was called a "SACH" foot, meaning solid-ankle, cushion-heel. It was fabricated of shoe-sole crepe rubber, laminated into layers and glued in sections over a hardwood keel. An important characteristic of this SACH foot was the presence of a soft heel cushion, of sponge rubber, that largely eliminated the above-indicated jolt and permitted the amputees to walk more naturally and with a greater degree of comfort.

Early in the 1960s, a greatly-improved SACH foot was developed and gradually became the most popular prosthetic foot in the U.S. It has a hardwood keel and a soft-foam heel cushion, but instead of being otherwise fabricated of shoe-sole crepe rubber, it is fabricated—around the keel—of a polyurethane foam the density of which is relatively high in comparison to the density of the heel cushion region.

Over the years, attempts have been made to improve the SACH foot still further. For example, some SACH feet were developed having flexible keels formed of metal or a synthetic resin, the keel being surrounded by foam synthetic resin. The purpose of the flexible keels is to store energy during the foot-flat and roll-over portions of the walking movement, followed by releasing of energy from the keel during toe-off. However, at least some of such SACH feet did not achieve commercial acceptance, or had problems relative to keel breakage and/or delamination of the interface between the keel and the synthetic resin foam.

SUMMARY OF THE INVENTION

The foot of the present invention has all of the advantages of the above-indicated popular SACH foot having a hardwood keel and, furthermore, has the advantages of energy storage in the keel during one part of the walking motion, and energy release from the keel during another part of the walking motion. Very importantly, the energy-storing and energy-releasing keel incorporated in the present elastomeric foam SACH foot does not present substantial breakage or delamination problems.

The SACH foot of the present invention comprises a body of synthetic resin foam elastomer the heel portion of which is softer than the remainder of the foam, such body of foam having embedded therin an articulated keel having substantially rigid links and also having energy-storing and energy-releasing elements between the links.

Stated more definitely, there are two pivotal flexible elements embedded in the keel, one below the metatarsal-phalangeal joints area and the other below the metatarsal-cuboid and metatarsal-cuneiforms joints area. These elements are flexible, compressible and elastomeric, and serve to store energy and thereafter release it as indicated above. The double-jointed keel allows the entire forefoot to yield (dorsiflex) in a limited manner in order to give a softer transition from heel contact to toe-off.

Between the underside of the keel and the upper region of the mass of foam elastomer that is disposed between the keel and the sole of the prosthetic foot, there is provided an inelastic flexible woven material which unitizes the keel links with each other and unitizes the keel with the underlying foam elastomer. The flexible woven material acts, furthermore, as hinges at the separation points between the rigid links.

The woven flexible material is connected to the keel links by both adhesive and screws. The underside of the woven flexible material bonds to the mass of elastomer therebeneath. At the bottom of such elastomer mass, there is a high density skin layer of elastomer in which is incorporated a fabric-mesh reinforcement.

DETAILED DESCRIPTION OF THE PREFERRED EMBODIMENT

Figure 1:
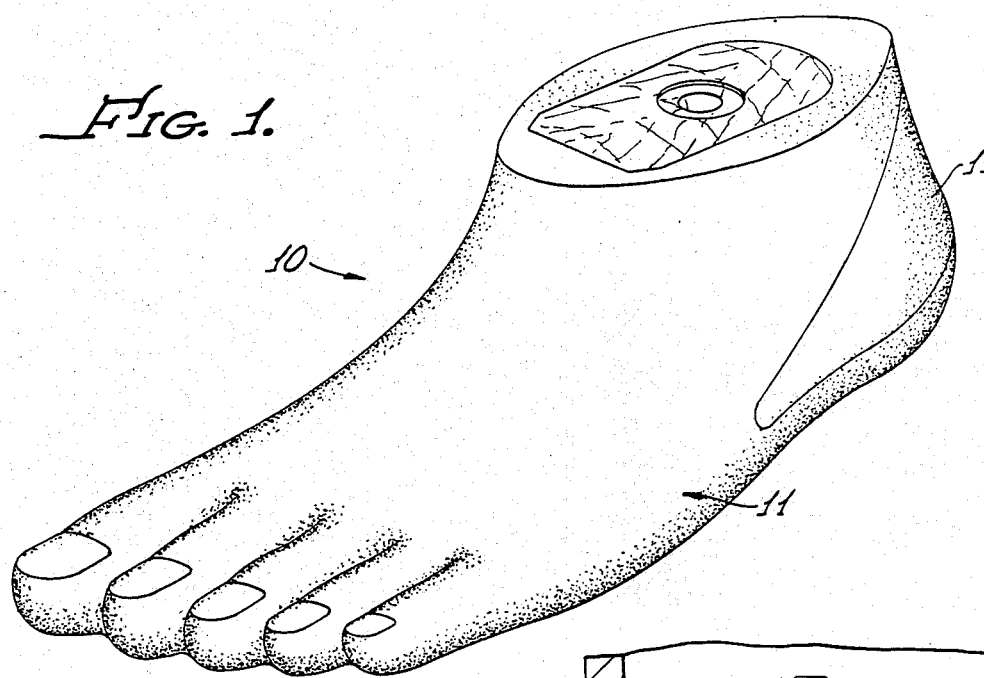
FIG. 1 is a top perspective view of the present prosthetic foot.
Figure 2:
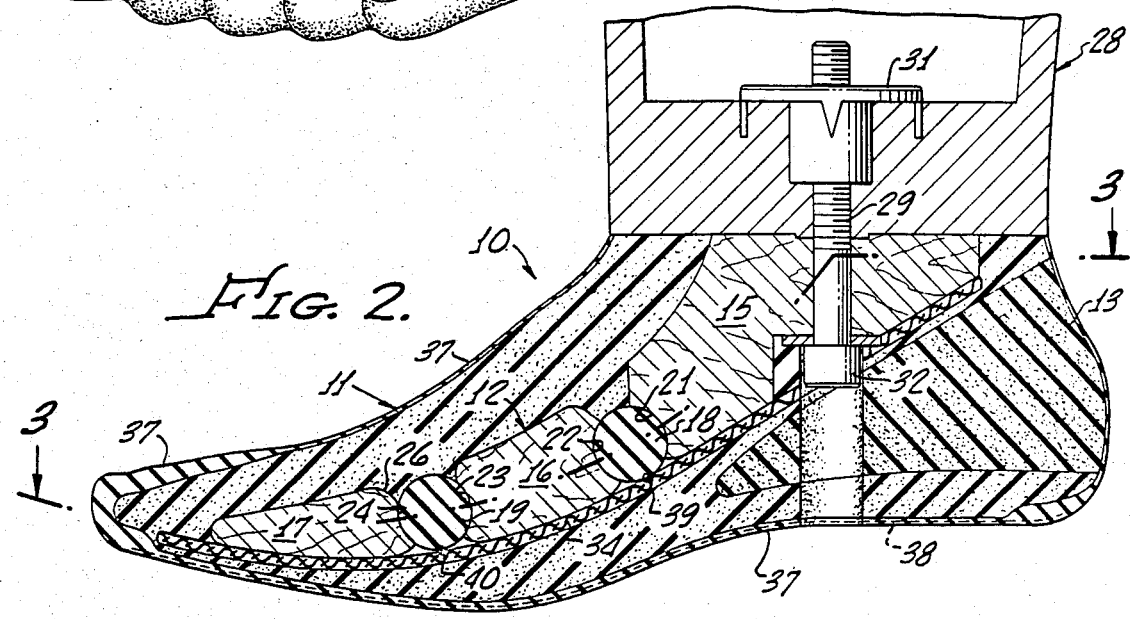
FIG. 2 is a longitudinal vertical sectional view of the foot, and further illustrating the attached portion of the prosthetic leg.
Figure 3:
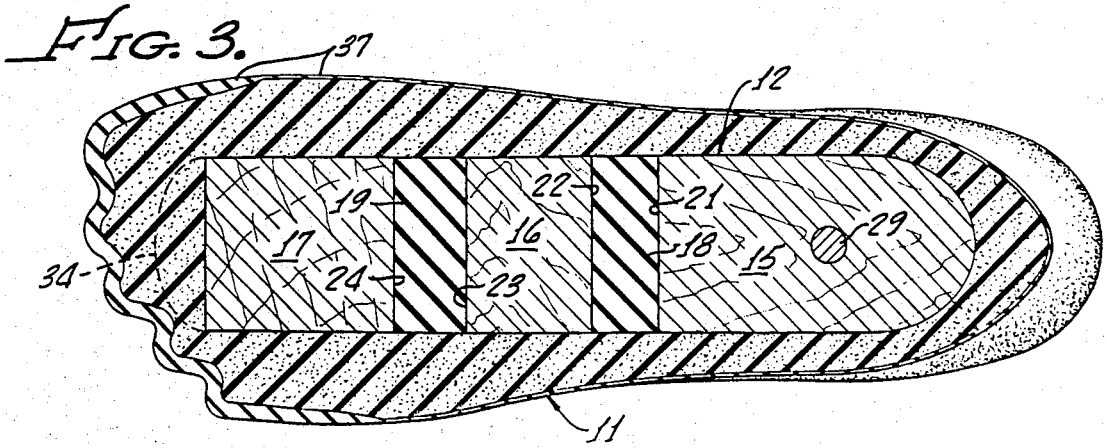
FIG. 3 is a fragmentary and generally horizontal sectional view taken on line 3—3 of FIG. 2.

Referring first to FIGS. 1 and 2, the present prosthetic foot is indicated generally at 10, and comprises a mass 11 of primarily foam elastomer that is resilient and flexible, and contains the energy-storing keel 12. The elastomeric mass 11 is preferably polyurethane, and is molded in a suitable mold shaped generally as a human foot, so that the prosthetic foot will have a natural appearance and the ability to fit naturally and perform naturally (without pinching) within shoes, sandles, stockings and socks. The keel 12 is present in the mold during the molding of the elastomeric mass 11, so as to be embedded in such mass to perform the functions indicated above and below.

A generally wedge-shaped heel region 13 of mass 11 is provided beneath the rear portion of keel 12, and is normally much softer than the remainder of the interior of the elastomeric mass. For example, wedge-shaped region 13 may have a hardness of from 15 to 40 durometer (A scale), depending upon the preference of the user, whereas the remainder of mass 11 (except at the skin indicated below) may have a hardness of about 35 to about 40 durometer (A scale). Except at heel region 13, the foam elastomer that forms the main body of mass 11 is quite dense.

There will next be described the energy-storing articulated keel 12 which cooperates with the elastomeric mass 11 to form a relatively natural prosthetic foot having the ability to flex about horizontal axes, and when thus flexed to store energy and thus generate a spring-back effect that adds markedly to the performance, fatigue resistance, and comfort of the foot.

Keel 12 has three substantially rigid links 15-17 preferably formed of hardwood such as hard-rock maple. Link 15 is the rear link and occupies the ankle region of the prosthetic foot, above the soft wedge 13 and beneath the prosthetic leg portion described subsequently. Link 16, the center link, may be termed the metatarsal link, being disposed in the same general region as the metatarsal bones, longitudinally of the foot, but being disposed much farther from the upper foot surface than are metatarsal bones. Link 17, the forward link, may be called the toe link because it projects forwardly into the inner portions of the toes of the prosthetic foot.

Stated more specifically, the forward end portion of the second link 16 is disposed in the vicinity of the metatarsal-phalangeal joints of a nonprosthetic foot having substantially the same size as the prosthetic foot. The rear end portion of such link 16 is disposed generally in the region where the metatarsal bones, or a nonprosthetic human foot of such same size, join the cuboid and cuneiform bones. However, the second or metatarsal link 16 is disposed far lower in the prosthetic foot than are the metatarsal bones in a nonprosthetic foot, relative to the upper skin surface of the foot. Thus, in the prosthetic foot there is a thick layer of foam elastomer above link 16.

The links 15-17 are associated with flexible, compressible, resilient elements 18 and 19, preferably cylinders, of elastomeric material. The rear cylinder, numbered 18, fits into complementary partial-cylindrical seats 21 and 22 formed, respectively, at the forward end of ankle link 15 and at the rear end of metatarsal link 16. The interfaces between the rear cylinder 18 and seats 21, 22 are preferably adhered to each other. Similarly to the cylinder 18 and the relationship thereof to its associated links 15, 16, the cylinder 19 fits into complementary partial-cylindrical seats 23, 24 formed, respectively, in metatarsal link 16 and toe link 17. Again, the interface regions of cylinder 19 and links 16, 17 are preferably adherent.

As in the case of the other elastomeric elements of the foot, the cylinders 18 and 19 are preferably polyurethane. Rear cylinder 18 is not foam but solid, while forward cylinder 19 is either solid or slightly-foamed material. It is emphasized that the cylinders 18, 19 are formed of such substance, and are sufficiently large in diameter, to store major amounts of energy. Each cylinder has a diameter of, for example, about ½ inch to about 1 inch, preferably about ¾ inch. Such cylinder diameters are also sufficiently large to space the links 15-17 substantial distances from each other, and insure that no portion of any link ever comes into contact with any portion of an adjacent link.

The cylinder 18 between the ankle and metatarsal links 15, 16 is quite hard, the preferred hardness being about 70 to about 80 durometer (A scale). The relatively hard cylinder 18 insures against drop-off (excessive forward moment of the prosthetic lower leg). The forward cylinder 19, between the metatarsal and toe links 16 and 17, is less hard, being preferably in the range of about 40 to about 50 durometer (A scale). Thus, there is a much greater resistance to flexing of metatarsal link 16 relative to ankle link 15 than there is to flexing of toe link 17 relative to metatarsal link 16. These two joints provide actions which store significant amounts of energy between the links while simulating, in a relatively natural manner, the pivotal actions which occur at both ends of the metatarsal bones of a nonprosthetic foot.

Figure 5:
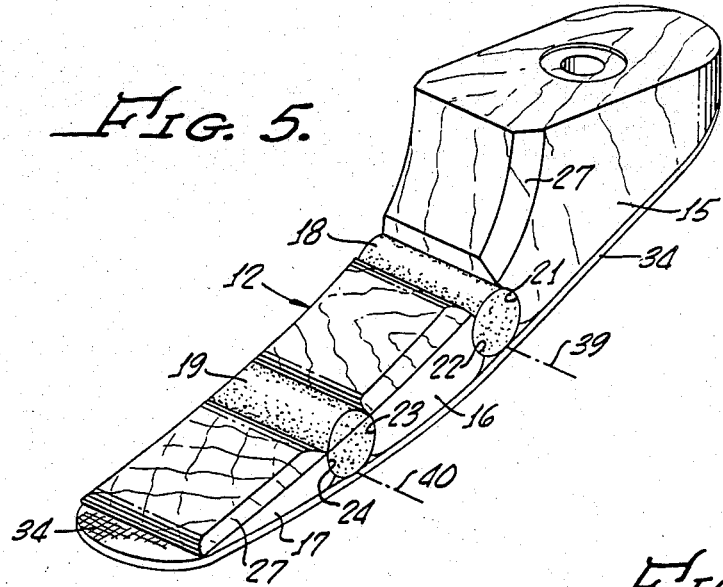
FIG. 5 is a top perspective view showing only the keel.

Links 15-17 have upper and lower surfaces that, as shown in FIG. 2, are forwardly convergent relative to each other. Thus, the forward end of toe link 17 is relatively thin. Above and below the various seats 21-24, the adjacent ends of links 15-17 are provided with beveled faces 26 which cooperate with exposed regions of cylinders 18, 19 to receive portions of the elastomeric mass 11 during the molding process. Beveled faces are also provided, as indicated at 27 in FIG. 5, at the upper corners of the links 15-17, these faces also being engaged by the elastomeric mass 10 after molding of such mass has occurred.

Figure 4:
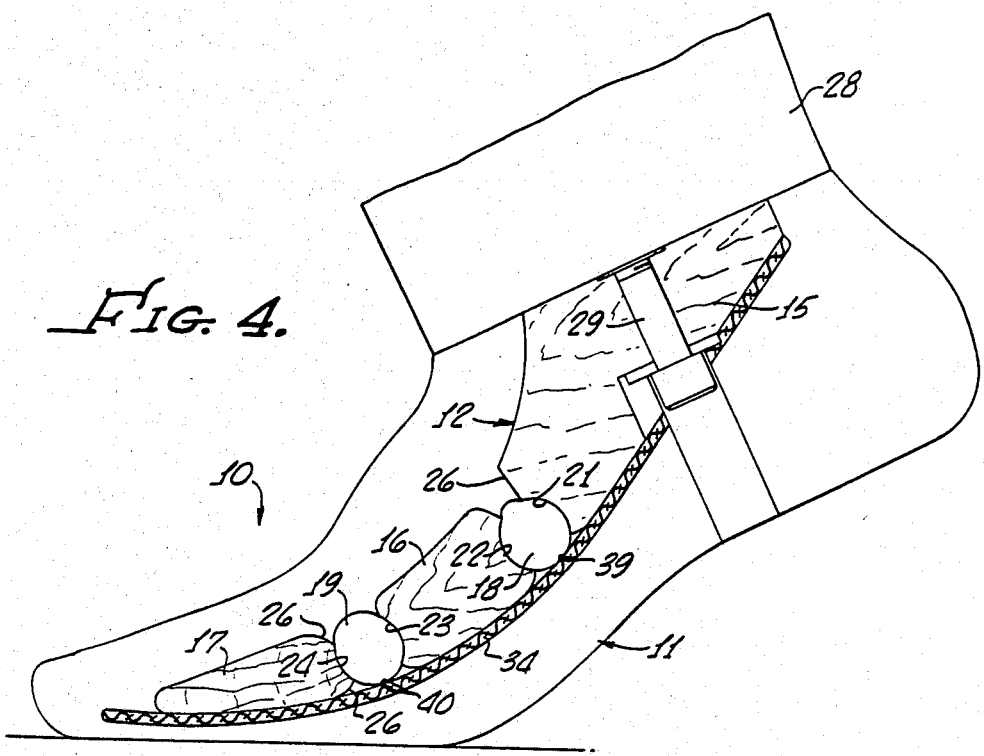
FIG.4 is a schematic view corresponding generally to major portions of FIG. 2, but showing the foot in its substantially fully-flexed condition present just before toe-off.

Ankle link 15, which is by far the largest of the links, is rigidly secured—in the SACH foot—to the lower end of a prosthetic leg 28, indicated in FIGS. 2 and 4. Thus, a bolt 29 is extended upwardly through a bore in rear link 15 and an associated bore in leg 28 into a hollow portion of such leg. A T-nut 31 is anchored in such hollow portion at the lower end of the leg, in the illustrated exoskeletal prosthesis. (In an endoskeletal prosthetic leg the connection would be suitably modified.) The head 32 of bolt 29 is disposed in a counterbore in ankle link 15, there being a flat washer and lock washer between the bolt head and the upper wall of the counter bore. When the bolt is tightened, the upper surface of ankle link 15 is seated snugly against the bottom end of leg 28, and the surrounding region of mass 11 fits snugly against the leg. The bolt is tightened or loosened by a wrench inserted through a vertical passage, not shown, in mass 11 coaxially of the bolt.

The ankle link 15 having been fixedly associated with the lower end of the prosthetic leg 28, there will next be described the means by which the metatarsal link 16 and toe link 17 are pivotally and resiliently associated with ankle link 15 so that the prosthetic foot will be properly associated with leg 28 and with the body of the user. The link association is effected in at least two- and preferably three-ways. Firstly, the mass of elastomeric foam, which is a relative high-density foam as indicated above, performs important functions of containing and resiliently connecting the links with each other, and of resiliently resisting pivotal and twisting motions. Secondly, there is securely associated with the underside of keel 12 a high-strength woven flexible material which may be referred to as belting and which is indicated generally at 34. Such belting 34 is preferably highly-flexible four-ply woven cotton. Thirdly, the cylinders 18, 19 are preferably adherently associated with the link seats 21-24 as stated above.

Figure 6:
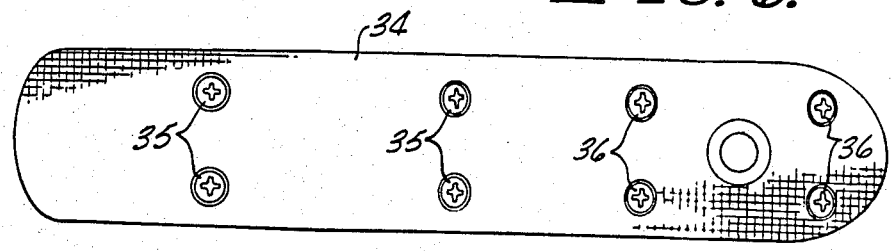
FIG. 6 is a bottom plan view of the keel of FIG. 5.

Except in the vicinity of the forward end of toe link 17, the shape and width of belting 34 preferably correspond to the shape and width of the underside of keel 12. Thus, as shown in FIG. 6, the rear end of the belting is rounded to correspond to a generally cylindrical surface portion at the rear side of ankle link 15. The forward end of belting 34 is likewise rounded, but such forward end extends forwardly from toe link 17, the latter end being preferably cut off square.

The upper surface of belting 34 is adhesively secured, preferably by epoxy, to the underside of each link 15-17. Furthermore, fastener means, namely, elongated screws 35 (FIG. 6), are inserted upwardly through the belting and threaded into the respective links 15-17. Preferably, the screws 35 are flush-head screws that recess into the lower regions of the belting. The flush-head screws preferably are associated with finishing washers.

The underside of the belting is associated with the region of elastomeric mass 12 therebeneath because the elastomeric material adheres thereto, particularly since such material penetrates somewhat into the small recesses at the underside of the belting and which result from the woven nature thereof.

It was stated above that the mass 11 is "primarily" foam elastomer. Stated more definitely, all portions of mass 11 are foam elastomer excepting a skin layer 37 which is provided exteriorly on the foot. Furthermore, flexible webbing material is incorporated in the skin at the bottom or sole region of the foot, in order to strengthen it and make it more wear resistant. Such flexible webbing is indicated at 38 in FIG. 2. The skin layer 37 is, although elastomeric and flexible, quite hard, preferably in the range of 70-80 durometer (A scale).

OPERATION

The combination of the present energy-storing keel 12 and elastomeric mass 11, which mass also stores a substantial amount of energy, enables the amputee to walk or run with more comfort and less energy expenditure than when a conventional SACH foot is employed. The keel 12 simulates the metatarsal bones and the metatarsal joints in their structures and fuctions as the foot contacts and separates from the ground. The enclosing elastomeric mass 11, including both the internal foam elastomer and the external skin layer, greatly strengthens the keel and provides resilient resistance to flexing and twisting actions.

It is emphasized that the present foot can both flex and twist, the twisting being either inversion or eversion. In the preferred form, where cylinders 18 and 19 are adhered to the links, both the cylinders and the surrounding mass resiliently resist twisting.

During walking and running, energy is stored upon roll-over on the toes (while the leg inclines further forwardly during walking), the storage being effected primarily by the compression of the two elastomeric cylinders 18, 19 embedded in keel 12 between the links 15-17 thereof. The cylinders 18, 19, in combination with other elements, provide a greatly improved spring action upon toe-off. Very preferably, the present keel is double-jointed, and allows the entire forefoot to yield (dorsiflex) in a limited but substantial manner. This generates a softer transition from heel contact (when the heel first touches the ground during walking) to toe-off.

During normal walking and running, the cylinders 18, 19 are loaded in compression and subsequently unload to greatly augment the spring action of the prosthetic foot. Stated more definitely, when the prosthetic foot is approaching the termination of the stance phase of walking or running actions, the ankle and metatarsal links 15, 16 pivot relative to each other at an axis 39 that extends through the belting. Furthermore, the metatarsal and toe links 16, 17 pivot relative to each other at a second axis 40. Both such axes are horizontal, and extend perpendicular to the foot. Pivoting is effected because of bending of belting 34 at such axes as shown by FIGS. 2 and 4, the former of which illustrates the foot flat on the ground and the latter of which shows the foot just prior to toe-off. At toe-off, when the foot separates from the ground, the foot springs back to its FIG. 2 position because of the stored energy in cylinders 18, 19 and, additionally, because of energy stored in the regions of elastomeric mass 11 adjacent the central and forward regions of keel 12.

When the walking or running is not conventional but is instead, for example, along the side of a hill, so as to tend to create a twisting motion (inversion or eversion) in the foot about an axis that extends generally longitudinally of the foot, the energy stored in cylinders 18 and 19 has components other than compressive, for example, torsional.

During all of these motions, the belting 34, the screws 35, the adhesive between belting and links, and the surrounding foam elastomer, hold the links in desired relationships and resist delamination or other breakdown of the foot. It has been found that the present prosthetic foot resists to a high degree delamination below the metatarsal and toe links 16, 17, both between such links and the belting 34 and between the belting and the elastomer therebeneath. There is also no substantial delamination below the ankle link 15, this region being subjected to less stresses than the regions below the metatarsal and toe links.

There has thus been provided high-strength, long-lasting, practical SACH foot that generates major advantages relative to reduced energy expenditure and enhanced comfort, while at the same time being aesthetically satisfactory and practical for wear with various types of footwear. As with the case of prior art SACH feet, the present prosthetic foot is adapted to be shaped in various ways, depending upon foot size, and upon heel height of the shoe, boot or sandle to be worn, and other factors. Furthermore, as in other SACH feet, the prosthetist and the amputee determine such factors as the degree of softness of the heel region 13 of the elastomeric mass 11. Furthermore, by providing different hardnesses and sizes of cylinders 18, 19 the present foot may be adapted for use by persons having greatly varying weights and athletic propensities, all as desired to make the present SACH foot highly satisfactory to the amputees.

Some of the advantages of the present invention may be obtained by providing, in the present combination, a keel having a number of joint regions other than two. Thus, there may be one or three, but these forms are not preferred.

The foregoing detailed description is to be clearly understood as given by way of illustration and example only, the spirit and scope of this invention being limited solely by the appended claims.

What is claimed is:

1. A prosthetic foot, which comprises:
   (a) a mass of resilient flexible elastomer formed into the general shape of a human foot, and
   (b) an articulated keel contained in said mass,
   said keel having at least two links,
   said keel having energy-storing resilient means at adjacent ends of said links,
   said energy-storing resilient means being so related to said links as to store energy when a forward link pivots upwardly relative to the link rearwardly adjacent thereto, as the stance phase of a walking or running movement is approached, and then during toe-off to release energy and cause such forward link to pivot downwardly relative to said link rearwardly adjacent thereto,
   said resilient means and said mass cooperating with each other to alternately store and release energy during walking and running.

2. The invention as claimed in claim 1, in which said mass (a) is a relatively dense and hard foam elastomer at the portions thereof forwardly of the ankle region of the prosthetic foot.

3. The invention as claimed in claim 1, in which said keel is fixedly connected at the rear portion thereof to the lower end of a prosthetic leg, and in which said mass of elastomer is relatively soft in the region below said rear portion, whereby said prosthetic foot is a SACH foot.

4. The invention as claimed in claim 1, in which said mass of resilient flexible elastomer has a nonfoam skin layer and a foam interior.

5. A prosthetic foot, which comprises:
   (a) a mass of resilient flexible elastomer molded into the general shape of a human foot,
   (b) a first keel link molded into said mass and embedded therein,
   said first link being adapted to be fixedly connected to the lower end of a prosthetic leg,
   (c) a second keel link disposed forwardly of said first keel link,
   said second link also being molded into said mass and being embedded therein,
   said second link being spaced sufficiently far from said first link that said links may pivot relative to each other about a horizontal pivot axis extending perpendicular to the prosthetic foot,
   (d) a length of strong, flexible belting embedded in said mass and disposed beneath said first and second links,
   (e) means to connect said belting to said first and second links to form a joint therebetween,
   said joint incorporating said pivot axis at a region of said belting between said links, and
   (f) energy-storing compressible means disposed above said belting and between adjacent ends of said links,
   said energy-storing compressible means occupying space between said links so as to be compressed between the ends of said links when said second link pivots upwardly relative to said first link as the stance phase of a walking or running motion is approached,
   said energy-storing compressible means releasing energy during toe-off,
   said energy-storing compressible means and said mass of resilient flexible elastomer cooperating with each other in alternately storing and releasing energy during walking and running motions so as to reduce fatigue and enhance comfort of the amputee.

6. The invention as claimed in claim 5, in which said mass (a) is foam elastomer having a nonfoam skin layer, in which said foam elastomer is relatively soft below at least the rear portion of said first link, and in which said foam elastomer is relatively dense above and below at least said second link.

7. The invention as claimed in claim 5, in which said energy-storing compressible means (f) is a mass of hard resilient elastomer.

8. The invention as claimed in claim 5, in which said links are formed of hardwood and said belting is formed of woven material.

9. The invention as claimed in claim 5, in which adjacent ends of said first and second links are shaped as partial-cylindrical faces, the axes of which extend horizontally and perpendicular to the prosthetic foot, in which said energy-storing compressible means (f) is a cylinder of hard resilient elastomer, and in which said cylinder seats on both of said faces.

10. The invention as claimed in claim 9, in which said cylinder is adherently associated with said faces.

11. The invention as claimed in claim 5, in which a flexible webbing material is molded into the skin portion of said mass of elastomer at the sole of the prosthetic foot.

12. The invention as claimed in claim 5, in which said first and second links are embedded deeply into said mass of elastomer, being spaced a substantial distance downwardly from the upper portion of the prosthetic foot and a substantial distance upwardly from the sole thereof.

13. The invention as claimed in claim 5, in which said energy-storing compressible means between adjacent ends of said links has a hardness in the range of about 40 to about 80 durometer (A scale), and in which the interior of said mass of said elastomer has a hardness, forwardly of the ankle region of the prosthetic foot, in the range of about 35 to about 40 durometer (A scale).

14. An energy-storing molded prosthetic SACH foot, which comprises:
   (a) a first keel link disposed in the ankle region of the foot and formed of strong rigid material,
   (b) a second keel link disposed forwardly of said first link,
   (c) a third keel link disposed forwardly of said second link,
   (d) strong flexible inelastic belting material disposed immediately beneath said first, second and third keel links,
   (e) means to connect said belting material to said links to effect inelastic connections therebetween,
   said belting material pivoting at regions between said links, during walking and running actions of the amputee, about horizontal axes extending perpendicularly to the foot through portions of said belting material between said links,
   (f) a first energy-storing compressible element disposed between said first and second links above said belting material and adapted to be compressed therebetween when said second link pivots upwardly relative to said first link, (g) a second energy-storing compressible element disposed between said second and third links above said belting material and adapted to be compressed therebetween when said third link pivots upwardly relative to said second link, and (h) a mass of flexible resilient elastomer molded around said keel in the general shape of a human foot, said elastomeric mass embedding said keel and said belting material, said elastomeric mass being thick both above and below said keel except at the upper part of the ankle region of said keel, said elastomeric mass being soft below said first link and being relatively hard above and below said second and third links and forwardly of said third link.

15. The invention as claimed in claim 14, in which said elastomeric mass (h) is foam elastomer having a nonfoam skin coating therearound.

16. The invention as claimed in the claim 15, in which the forward end portion of said second link is disposed in the vicinity of the metatarsal-phalangeal joints of a nonprosthetic foot having substantially the same size as the prosthetic foot, and in which the rear end portion of said second link is disposed generally at the joints where the metatarsal bones join the cuboid bone and the cuneiform bones of a nonprosthetic human foot having generally the same size as the prosthetic foot, except that said second link is disposed far lower in said prosthetic foot than are the metatarsal bones in a nonprosthetic foot relative to the upper skin surface of the foot.

17. The invention as claimed in claim 15, in which said third link extends forwardly to a forward end that is located in the base regions of the toe portions of said elastomeric mass (h).

18. The invention as claimed in claim 15, in which said belting is a single piece that extends forwardly from said first link to said third link and then forwardly fron said third link, and is embedded in said mass of elastomer forwardly of said third link.

19. The invention as claimed in claim 15, in which said links are formed of hardwood, and in which said elastomer is polyurethane.

20. The invention as claimed in claim 15, in which a prosthetic leg is provided, and in which said prosthetic foot is combined with said prosthetic leg, and in which means are provided to effect a rigid inflexible connection between said prosthetic foot and prosthetic leg, said means being located at said first link.

21. The invention as claimed in claim 15, in which said first compressible element has the hardness in the range of about 70 to about 80 durometer (A scale), and in which said second compressible element has a hardness in the range of about 40 to about 50 durometer (A scale).

22. The invention as claimed in claim 14, in which said mass of elastomeric material has a nonfoam skin layer the hardness of which is in the range of about 70 to about 80 durometer (A scale), and has an interior high-density foam layer the hardness of which is in the range of about 35 to about 40 durometer (A scale) in the regions above and below said second and third links, and in which the region of said mass below said first link is a relatively low-density foam.

23. The invention as claimed in 15, in which the foam interior of said elastomeric mass extends into the spaces between said links and into contact with said energy-storing compressible means.

24. The invention as claimed in claim 15, in which said first and second energy-storing compressible means are cylinders of high-density elastomer, said cylinders being seated in shallow grooves formed at the ends of said links adjacent said cylinders, said cyliners having diameters sufficiently large to permit a substantial degree of pivoting of said links relative to each other, and to provide a large amount of energy storage and energy release during such pivoting.

25. The invention as claimed in claim 15, in which said links have beveled or inclined faces at the upper regions thereof, and in which said belting material is woven cotton material secured by both adhesive and screws to all of said links.

26. The invention as claimed in claim 15, in which the means to connect said belting material to said links comprises adhesive therebetween and further comprises screws extending through said belting material and into said links.

27. The invention as claimed in claim 15, in which said first energy-storing element (f) is greatly more pivot resistant than is said second energy-storing element (g).

28. The invention as claimed in claim 15, in which said energy-storing compressible elements (f) and (g) are cylinders the diameters of which are about ½ inch to about 1 inch.

* * * * *

UNITED STATES PATENT AND TRADEMARK OFFICE
CERTIFICATE OF CORRECTION

PATENT NO. : 4,652,266

DATED : March 24, 1987

INVENTOR(S) : James D. Truesdell

It is certified that error appears in the above-identified patent and that said Letters Patent is hereby corrected as shown below:

On the cover page, delete "Placentia" from the Assignee's address and substitute therefor ---Costa Mesa---.

Line 2 of the Abstract, delete both occurrences of "heel" and substitute therefor ---keel---.

Claim 24 (column 10, line 26), delete "cyliners" and substitute therefor ---cylinders---.

Signed and Sealed this

Eighteenth Day of August, 1987

Attest:

DONALD J. QUIGG

*Attesting Officer*     *Commissioner of Patents and Trademarks*